United States Patent
Yock et al.

(10) Patent No.: US 10,420,557 B2
(45) Date of Patent: Sep. 24, 2019

(54) SKIN STRAINING DEVICES AND METHODS

(71) Applicant: Neodyne Biosciences, Inc., Menlo Park, CA (US)

(72) Inventors: Paul Yock, Atherton, CA (US); Reinhold H. Dauskardt, Menlo Park, CA (US); Jasper Jackson, Newark, CA (US); John A. Zepeda, Los Altos, CA (US); William R. Beasley, Los Altos, CA (US)

(73) Assignee: Neodyne Biosciences, Inc., Menlo Park, CA (US)

( * ) Notice: Subject to any disclaimer, the term of this patent is extended or adjusted under 35 U.S.C. 154(b) by 443 days.

(21) Appl. No.: 15/169,572

(22) Filed: May 31, 2016

(65) Prior Publication Data

US 2017/0020522 A1    Jan. 26, 2017

Related U.S. Application Data

(63) Continuation of application No. 13/029,023, filed on Feb. 16, 2011, now Pat. No. 9,358,009, which is a continuation-in-part of application No. 12/854,859, filed on Aug. 11, 2010, now Pat. No. 8,592,640.

(51) Int. Cl.
　　*A61F 13/00*　　(2006.01)
　　*A61B 17/08*　　(2006.01)
　　*A61B 90/00*　　(2016.01)

(52) U.S. Cl.
CPC ............ *A61B 17/085* (2013.01); *A61B 17/08* (2013.01); *A61B 90/02* (2016.02); *A61B 2017/081* (2013.01)

(58) Field of Classification Search
CPC ... A61B 17/08; A61B 2017/081; A61B 90/02; A61B 90/03; A61B 19/24; A61B 17/0057; A61B 17/0049; A61B 17/02; A61F 13/00
USPC ...................................... 602/41, 53
See application file for complete search history.

(56) References Cited

U.S. PATENT DOCUMENTS

| | | | |
|---|---|---|---|
| 114,750 A | 5/1871 | Battersby |
| 363,538 A | 5/1887 | Penny |
| 633,050 A | 9/1899 | Spenard |
| 1,074,413 A | 9/1913 | Baun et al. |
| 1,774,489 A | 8/1930 | Sarason |
| 1,969,188 A | 8/1934 | Spicer |
| 2,018,517 A | 10/1935 | Fetter |
| 2,303,131 A | 11/1942 | Morgan |

(Continued)

FOREIGN PATENT DOCUMENTS

| | | |
|---|---|---|
| CA | 2321491 A1 | 9/1999 |
| CA | 2621387 A1 | 3/2007 |

(Continued)

OTHER PUBLICATIONS

3M Healthcare (May 2004). "Tips for Trouble-Free Taping," 3M HealthCare: St. Paul, MN, four pages.

(Continued)

*Primary Examiner* — Kim M Lewis
(74) *Attorney, Agent, or Firm* — Dorsey & Whitney LLP

(57) ABSTRACT

A skin frame or other skin straining device strains skin on each side of a wound where a wound has been closed to off load stresses at the wound site. A dressing may be applied to the strained skin. The dressing may be integral with one or more elements of the skin straining device.

19 Claims, 12 Drawing Sheets

(56) References Cited

U.S. PATENT DOCUMENTS

| | | |
|---|---|---|
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-sierra et al. |
| 4,073,298 A | 2/1978 | Le |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schaefer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do |
| 6,570,051 B1 | 5/2003 | Beaudry |
| 6,572,878 B1 | 6/2003 | Blaine |
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 * | 3/2010 | Gurtner ............... A61L 15/42 523/111 |
| 7,834,232 B2 | 11/2010 | Rastegar et al. |
| RE42,126 E | 2/2011 | Ye et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,248,048 B2 | 2/2016 | Jackson et al. |
| 9,248,049 B2 | 2/2016 | Gurtner et al. |
| 9,248,051 B2 | 2/2016 | Gurtner et al. |
| 9,358,009 B2 | 6/2016 | Yock et al. |
| 9,492,329 B2 | 11/2016 | Zepeda et al. |
| 2002/0013300 A1 | 1/2002 | Capelli-schellpfeffer |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |

(56) References Cited

U.S. PATENT DOCUMENTS

| | | |
|---|---|---|
| 2003/0220700 A1 | 11/2003 | Hammer et al. |
| 2004/0059280 A1 | 3/2004 | Makower et al. |
| 2004/0236360 A1 | 11/2004 | Cohn et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0129776 A1 | 6/2007 | Robins et al. |
| 2007/0142761 A1 | 6/2007 | Aali |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0051687 A1 | 2/2008 | Rogers |
| 2008/0208098 A1 | 8/2008 | Rennix |
| 2008/0228220 A1 | 9/2008 | Weiser |
| 2009/0177136 A1 | 7/2009 | Liedtke et al. |
| 2010/0056873 A1* | 3/2010 | Allen .................. A61B 5/01 600/300 |
| 2010/0191253 A1 | 7/2010 | Oostman, Jr. et al. |
| 2010/0280428 A1 | 11/2010 | Widgerow et al. |
| 2011/0152738 A1 | 6/2011 | Zepeda et al. |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0203273 A1 | 8/2012 | Riskin et al. |
| 2012/0209377 A1 | 8/2012 | Machold et al. |
| 2012/0221044 A1* | 8/2012 | Archibald ............ A61B 17/08 606/214 |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0184629 A1 | 7/2013 | Gurtner et al. |
| 2013/0190673 A1 | 7/2013 | Gurtner et al. |
| 2013/0281904 A1 | 10/2013 | Jackson et al. |
| 2014/0088481 A1 | 3/2014 | Jackson et al. |
| 2014/0135677 A1 | 5/2014 | Zepeda et al. |
| 2014/0135678 A1 | 5/2014 | Zepeda et al. |
| 2015/0141836 A1 | 5/2015 | Naumann et al. |
| 2016/0213522 A1 | 7/2016 | Gurtner et al. |
| 2017/0020522 A1 | 1/2017 | Yock et al. |
| 2017/0112673 A1 | 4/2017 | Jackson et al. |

FOREIGN PATENT DOCUMENTS

| | | |
|---|---|---|
| CN | 1414842 A | 4/2003 |
| CN | 1608604 A | 4/2005 |
| CN | 102665623 A | 9/2012 |
| EP | 2161011 A1 | 3/2010 |
| EP | 2464322 A2 | 6/2012 |
| JP | 2004515256 A | 5/2004 |
| JP | 2004223087 A | 8/2004 |
| JP | 2004536898 A | 12/2004 |
| JP | 2006513748 A | 4/2006 |
| JP | 2007537781 A | 12/2007 |
| JP | 2009545382 A | 12/2009 |
| JP | 2013501591 A | 1/2013 |
| RU | 2019138 C1 | 9/1994 |
| WO | 9717919 A1 | 5/1997 |
| WO | 9730700 A2 | 8/1997 |
| WO | 9730700 A3 | 10/1997 |
| WO | 0053139 A1 | 9/2000 |
| WO | 0139693 A2 | 6/2001 |
| WO | 0139693 A3 | 12/2001 |
| WO | 0215816 A2 | 2/2002 |
| WO | 0245698 A2 | 6/2002 |
| WO | 0245698 A3 | 7/2002 |
| WO | 02092783 A2 | 11/2002 |
| WO | 2002087645 A1 | 11/2002 |
| WO | 0215816 A3 | 10/2003 |
| WO | 2004060413 A1 | 7/2004 |
| WO | 02092783 A3 | 7/2005 |
| WO | 2005079674 A1 | 9/2005 |
| WO | 2005096981 A2 | 10/2005 |
| WO | 2005096981 A3 | 3/2006 |
| WO | 2006124671 A2 | 11/2006 |
| WO | 2006124671 A3 | 4/2007 |
| WO | 2008019051 A2 | 2/2008 |
| WO | 2008019051 A3 | 4/2008 |
| WO | 2011019859 A2 | 2/2011 |
| WO | 2011019859 A3 | 4/2011 |
| WO | 2012094648 A1 | 7/2012 |
| WO | 2012119131 A1 | 9/2012 |

OTHER PUBLICATIONS

3M Healthcare. (2001). "Reducing the Risk of Superficial Skin Damage Related to Adhesive Use," 3M HealthCare: St Paul, MN, two pages.

3M Healthcare. (2003). "Steri-Strip: Skin Closures," Product Insert, 3M HealthCare: St. Paul, MN, one page.

3M Healthcare. (2006). "3MTM Steri-StripTM S Surgical Skin Closure. The Simple, Non-Invase Alternative to Staples and Sutures from the Steri-Strip Family," HealthCare: St. Paul, MN, two pages.

3M Healthcare. (Date Unknown). "3M™ Steri-Strip™ S Surgical Skin Closure," 3M HealthCare: St. Paul, MN, one page.

3M Healthcare. (Date unknown). "3M™ Steri-Strip™ S Surgical Skin Closure. Poster of Available Sizes," 3M HealthCare: St Paul, MN, three pages.

3M Healthcare. (Jun. 27, 2002). "3M™ Steri-Strip™ Adhesive Skin Closures (reinforced): Commonly Asked Questions," 3M HealthCare: St Paul, MN, pp. 1-4.

3M Healthcare. (Oct. 19, 2006). "3M™ Steri-Strip™ S Surgical Skin Closure: Commonly Asked Questions," 3M Healthcare: St. Paul, MN, pp. 1-8.

3M Medical. (2006). "3MTM Steri-StripTM S Surgical Skin Closure. Patient Care Information," 3M HealthCare: St. Paul, MN, two pages.

3M Medical. (2007). "3MTM Steri-StripTM S Surgical Skin Closure. Application Examples, Comparisons and Results," 3M HealthCare: St. Paul, MN, four pages.

Anonymous (2003). "3MTM Steri-StripTM Adhesive Skin Closures," 3M HealthCare Brochure, twelve pages.

Anonymous. (2005). "3MTM TegadermTM Family of Transparent Dressings," 3M HealthCare Brochure, six pages.

Anonymous. (2006). "Avocet Polymer Technologies," located at <http://www.avocetcorp.com/index.html>, last visited on Nov. 5, 2007, one page.

Anonymous. (2006). "Avogel Scar Hydrogel," located at <http://www.avocetcorp.com/avogel_scar_hydrogel.html>, last visited on Nov. 5, 2007, two pages.

Anonymous. (2006). "Avosil Ointment," located at <http://www.avocetcorp.com/avosil.html>, last visited on Nov. 5, 2007, three pages.

Anonymous. (Date Unknown). "Mepiform Instructions of Use," Tendra Corporation Brochure, two pages.

Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.

Brace, "Definition of Brace", Merriam Webster, Available Online at <www.merriam-webster.com>, 2015, 4 pages.

Canica Design Inc. (Date Unknown). "ABRA® Abdominal Wall Closure Set," located at < http://www.canica.com/instructions/1D1544RA%20-%20ABRA%20CWK08%20IFU.pdf>, last visited on Sep. 10, 2009, pp. 1-11.

(56) References Cited

OTHER PUBLICATIONS

Canica Design Inc. (Date Unknown). "ABRA® Surgical Skin Closure Set," located at <http://www.canica.com/instructions/1D0830RH.pdf>, last visited on Sep. 10, 2009, pp. 1-4.
Extended European Search Report (includes Supplementary European Search Report and Search Opinion) received for European Patent Application No. 12752239.9, dated Oct. 1, 2014, 7 pages.
Extended European Search Report dated Aug. 19, 2013 for European Patent Application No. 10 808 724.8, filed on Aug. 11, 2010, 8 pages.
Extended European Search Report dated Feb. 23, 2016, for European Patent Application No. 13 825 488.3, filed on Feb. 8, 2013, 6 pages.
Extended European Search Report dated Jun. 19, 2017 for European Patent Application No. 16205575.0, filed Aug. 11, 2010, 8 pages.
Extended European Search Report received for European Patent Application No. 12732236.0, dated Jun. 29, 2015, 6 pages.
International Search Report and Written Opinion dated May 1, 2012, for PCT Patent Application No. PCT/US2012/020561, filed Jan. 6, 2012, three pages.
International Search Report and Written Opinion dated Feb. 7, 2008, for PCT Application No. PCT/US2007/017320, filed on Aug. 3, 2007, 11 pages.
International Search Report and Written Opinion dated Feb. 8, 2011, for PCT Patent Application No. PCT/US2010/045239, filed on Aug. 11, 2010, one page.
International Search Report and Written Opinion received for PCT Patent Application No. PCT/US2013/025449, dated Feb. 5, 2015, 8 pages.
International Search Report dated Jun. 28, 2012, for PCT Patent Application No. PCT/US2012/027618, filed Mar. 2, 2012, two pages.
International Search Report dated May 29, 2012, for PCT Patent Application No. PCT/US2012/25510, filed Feb. 16, 2012, three pages.
Mask, "Definition of Mask", Merriam Webster, Available Online at <www.merriam-webster.com>, 2015, 4 pages.
Nahabedian, M.Y. (Dec. 2005). "Scar Wars: Optimizing Outcomes with Reduction Mammaplasty," Plastic and Reconstructive Surgery, 116(7):2026-2029.
NHSSB Wound Management Manual, Northern Health and Social Services Board, 2005, pp. 1-97.
Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.
Smith & Nephew. (Date Unknown). "CICA-CARE. Silicone Gel Sheeting," located at <http://wound.smith-nepehew.com/za/Product/asp?NodeId=569&Tab=5&hide=True>, last visited on Jun. 9, 2009, one page.
Wound Care Technologies. (2008). "DERMACloseTM RC: Continuous External Tissue Expander, Brochure No. PL-0020-F," located at <http://www.woundcaretech.com/sell-sheet.pdf>, last visited on Sep. 10, 2009, two pages.
Wound Care Technologies. (2008). "Instructions for Use. DERMACloseTM RC, Brochure No. DR-0079-A," located at < http://www.dermaclose.com/instructions.pdf>, last visited on Sep. 10, 2009, two pages.
Written Opinion of the International Searching Authority dated Jun. 28, 2012, for PCT Application No. PCT/US2012/027618, filed Mar. 2, 2012, 10 pages.
Written Opinion of the International Searching Authority dated May 29, 2012, for PCT Application No. PCT/US2012/25510, filed on Feb. 16, 2012, 8 pages.
Office Action received in EP Application No. 16205575.0 dated Dec. 10, 2018, pp. all.
3M Medical. (2006). "They Say Every Scar Tells a Story," 3M HealthCare: St. Paul, MN, one page.

Aarabi, S. et al. (Oct. 2007). "Mechanical Load Initiates Hypertrophic Scar Formation Through Decreased Cellular Apoptosis," The FASEB Journal 21(12):3250-3261.
Al-Attar, A. et al. (Jan. 2006). "Keloid Pathogenesis and Treatment," Plastic and Reconstructive Surgery 117(1): 286-300.
Angelini, G.D. et al. (1984). "Comparative Study of Leg Wound Skin Closure in Coronary Artery Bypass Graft Operations," Thorax 39:942-945.
Atkinson, et al., (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116(6)., 1648-1656.
Bachert, B. et al. (2003). "Probing Elastic Modulus and Depth of a Two Layer Human Skin Model with Piezoelectric Cantilevers," Biomedical Engineering Senior Design Team, Drexel University, 27 pages.
Berman, B. et al. (Mar. 3, 2005). "Keloid and Hypertrophic Scar," located at <http://www.emedicine.com/DERM/topic205.htm>, last visited on Nov. 19, 2007, 23 pages.
Bunker, T.D. (1983). "Problems with the Use of Op-Site Sutureless Skin Closures in Orthopaedic Procedures," Annals of the Royal College of Surgeons of England 65:260-262.
Burd, A. et al. (Dec. 2005). "Hypertrophic Response and Keloid Diathesis: Two Very Different Forms of Scar," Plastic and Reconstructive Surgery 116(7):150-157.
Chen, H-H. et al. (Jul. 2001). "Prospective Study Comparing Wounds Closed With Tape With Sutured Wounds in Colorectal Surgery," Arch. Surg. 136:801-803.
Davison, S.P. et al. (Jan. 2006). "Ineffective Treatment of Keloids with Interferon Alpha-2b," Plastic and Reconstructive Surgery 117(1):247-252.
Escoffier, C. et al. (Sep. 1989). "Age-Related Mechanical Properties of Human Skin: An In Vivo Study," J. Invest. Dermatol. 9(3)3:353-357.
Evans, S.L. et al. (2009). "Measuring the Mechanical Properties of Human Skin in vivo Using Digital Correlation and Finite Element Modeling," J. Strain Analysis 44:337-345.
Fairclough, J.A. et al. (1987). "The Use of Sterile Adhesive Tape in the Closure of Arthroscopic Puncture Wounds: A Comparison with a Single Layer Nylon Closure," Annals of the Royal College of Surgeons of England 69:140-141.
Gorney, M. (Mar. 2006). "Scar: The Trigger to the Claim," Plastic and Reconstructive Surgery 117(3):1036-1037.
Hof, M. et al. (Jul. 2006). "Comparing Silicone Pressure-Sensitive Adhesives to Silicone Gels for Transdermal Drug Delivery," presented at 33 Annual Meeting and Exposition of the Controlled Release Society, Vienna, Austria, Jul. 22-26, 2006, seven pages.
Koval, K.J. et al. (Oct. 2003). "Tape Blisters Following Hip Surgery. A Prospective Randomized Study of Two Types of Tape," The Journal of Bone and Joint Surgery, 85-5(10):1884-1887.
Kuo, F. et al. (May 2006). "Prospective Randomized, Blinded Study of a New Wound Closure Film Versus Cutaneous Suture for Surgical Wound Closure," Dermatological Surgery 32(5):676-681.
Mustoe, T.A.,et al. (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116.6, 1657-1658.
O'Brien, L. et al. (2009). "Silicon Gel Sheeting for Preventing and Treating Hypertrophic and Keloid Scars," The Cochrane Collaboration, pp. 1-47.
Pitcher, D. (Feb. 1983). "Sutureless Skin Closure for Pacemaker Implantation: Comparison with Subcuticular Suture," Postgraduate Medical Journal 59:83-85.
Shirado, et al., "Realization of Human Skin-Like Texture by Emulating Surface Shape Pattern and Elastic Structure," presented at Symposium on Haptic Interfaces for Virtual Environment and Teleoperator Systems 2006, Mar. 25-26, 2006, Alexandria, VA, pp. 295-296.
Sullivan, et al., Sullivan, S.R. et al. (2007). "Acute Wound Care," Chapter 7 in ACS Surgery: Principles and Practice, 24 pages.

(56) References Cited

OTHER PUBLICATIONS

Téot, L. (2005). "Scar Control" European Tissue Repair Society, located at <http://www.etrs.org/bulletin12_1/section11.php>, last visited on Nov. 30, 2007, 13 pages.

Vaughan, et al., Vaughan, P. et al. (2006). "Optimal Closure of Surgical Wounds in Forefoot Surgery: Are Adhesive Strips Beneficial?" Acta Orthop. Belg. 72(6):731-733.

Vowden, K. (Mar. 2003). "Wound Management. Policy and Resource Pack," Bradford Teaching Hospitals NHS Foundation Trust, pp. 1-70.

Watson, G.M. (1983). "Op-Site Skin Closure: A Comparison with Subcuticular and Interrupted Sutures," Annals of the Royal College of Surgeons of England 65:83-84.

Webster, et al., Webster, D.J.T. et al. (Sep. 1975). "Closure of Abdominal Wounds by Adhesive Strips: A Clinical Trial," British Medical Journal 20:696-698.

Westaby, Westaby, S. (1980). "Evaluation of a New Product for Sutureless Skin Closure," Annals of the Royal College of Surgeons of England 62:129-132.

\* cited by examiner

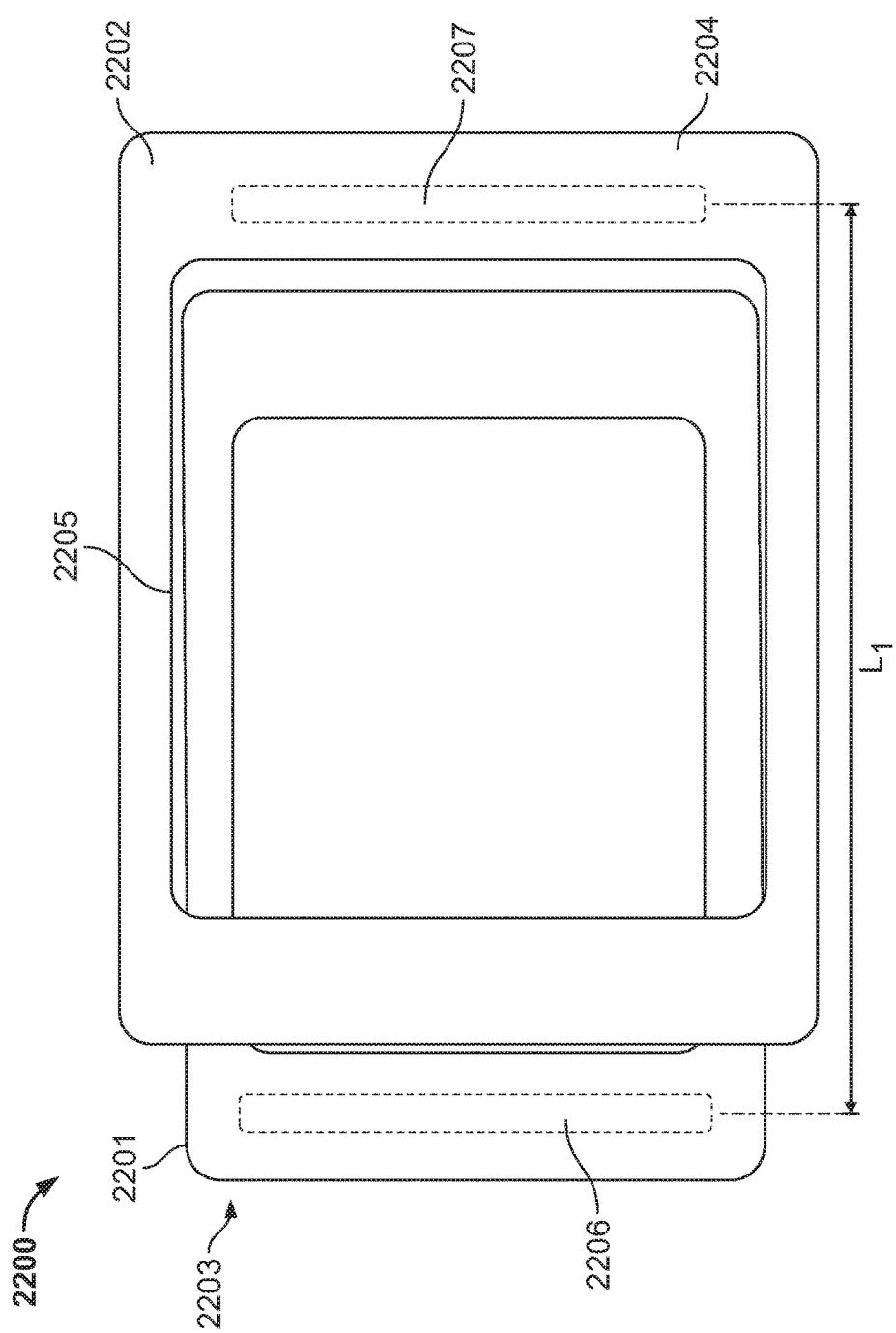

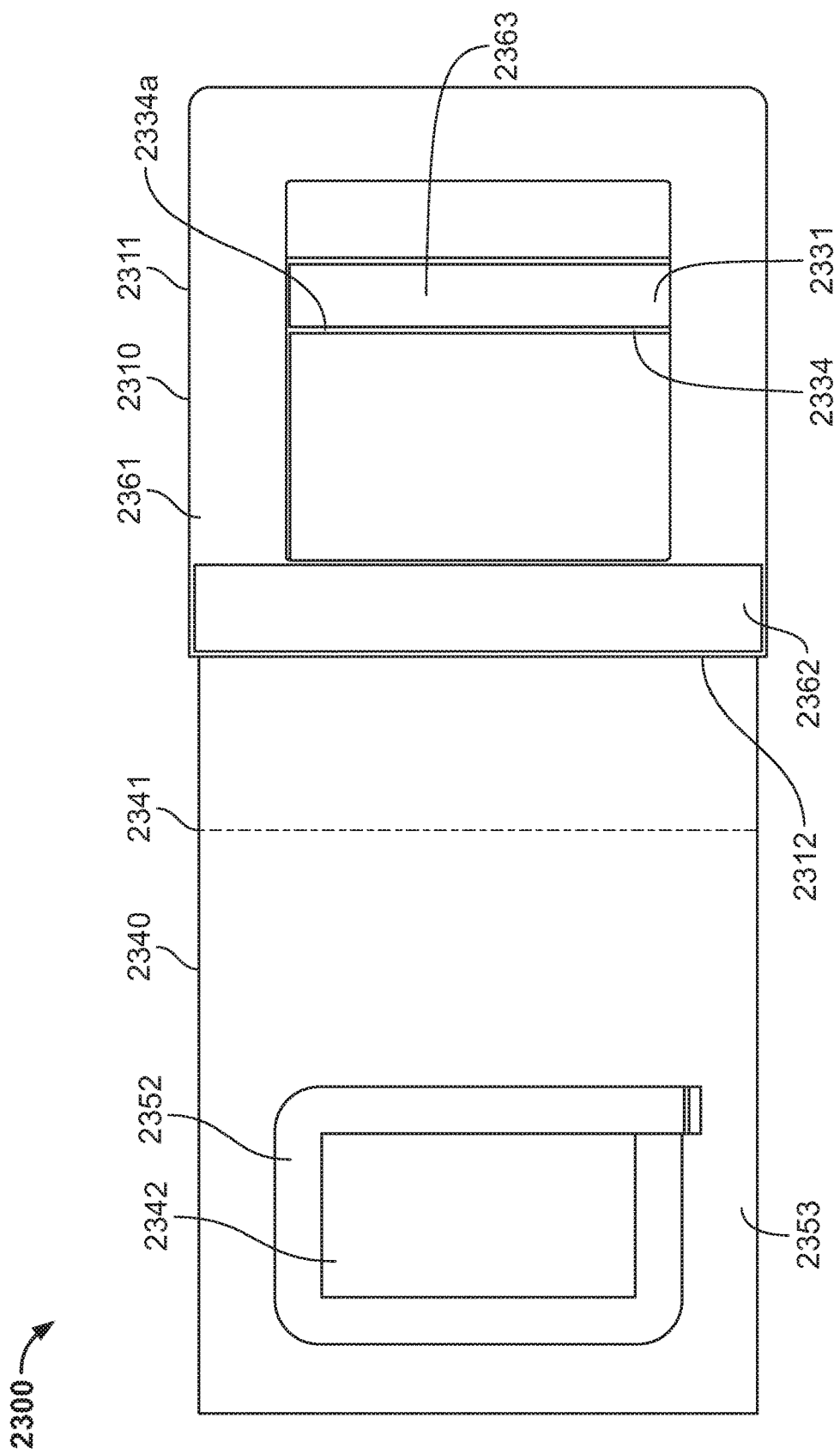

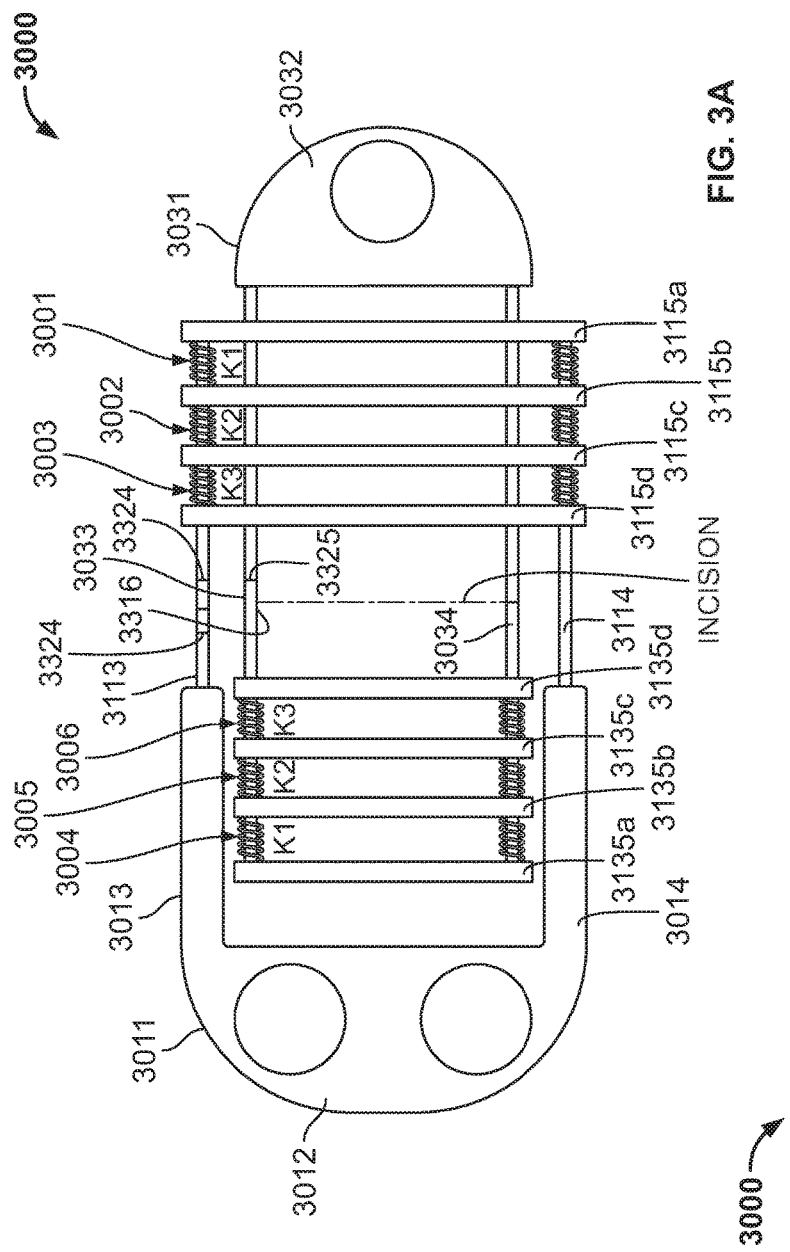
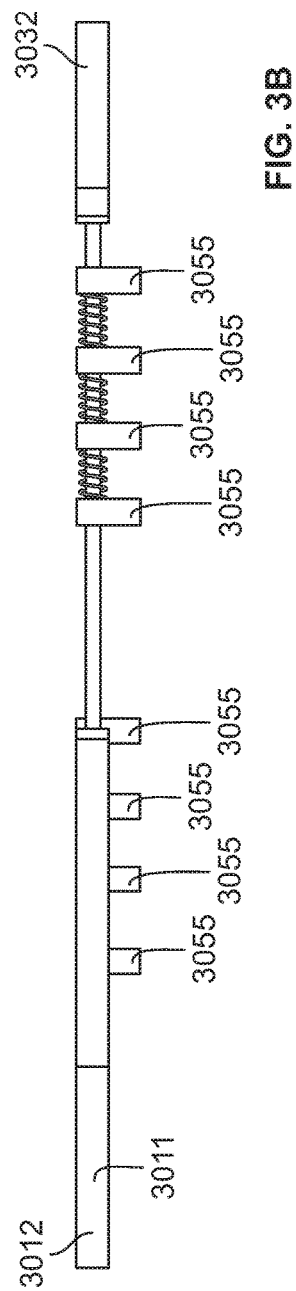
FIG. 3A
FIG. 3B

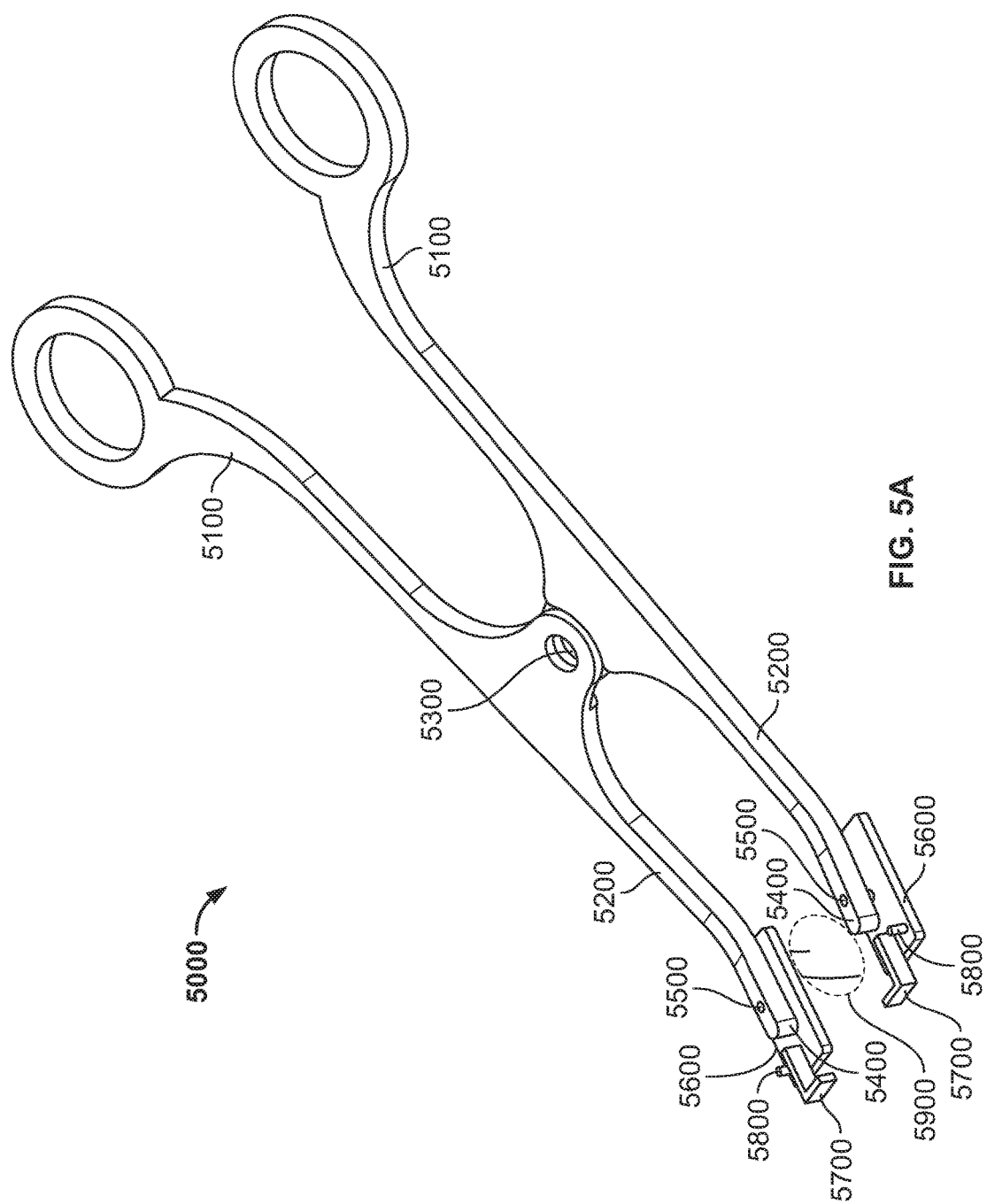

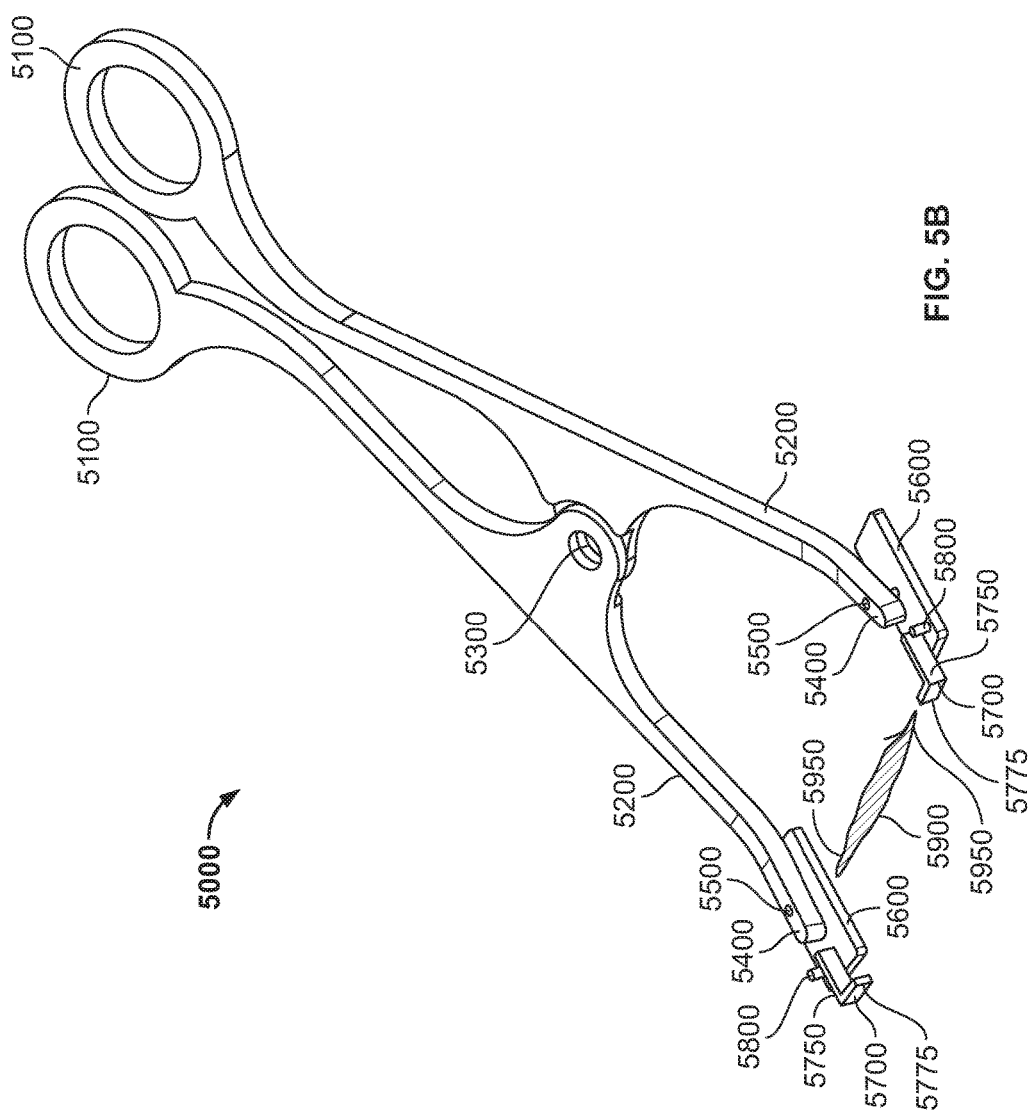

SKIN STRAINING DEVICES AND METHODS

CROSS-REFERENCE TO RELATED APPLICATIONS

This application is a continuation of U.S. application Ser. No. 13/029,023, filed on Feb. 16, 2011, which is a continuation-in-part of U.S. application Ser. No. 12/854,859, filed on Aug. 11, 2010, which is hereby incorporated by reference in its entirety. This application is also related to U.S. application Ser. No. 11/888,978, filed on Aug. 3, 2007, which is hereby incorporated by reference in its entirety.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

BRIEF SUMMARY

Devices, kits and methods described herein may be for wound healing, including the treatment, amelioration, or prevention of scars and/or keloids by applying and/or maintaining a strain, compression or stress in skin by to transferring a generally planar force from the device to the skin surface. Devices kits and methods herein may also include a dressing or other device that maintains the skin in a strained, compressed or stressed state to unload stresses on the skin at or near a wound site for a treatment period.

According to some variations, a skin frame or other skin straining device is provided that strains skin on each side of a wound to off load stresses at the wound site. A dressing may be applied to the strained skin. The dressing may be integral with one or more elements of the skin straining device.

According to some variations, a method of unloading stress experienced by skin or a wound of a subject comprises: straining skin on opposing sides of a treatment area wherein the treatment area comprises a previously closed wound; and applying a dressing to at least a portion of the treatment area to maintain at least a portion of the strain for a treatment period. According to some variations, the step of straining skin comprises straining skin to a measured amount. According to some variations, the step of straining skin to a measured amount comprises straining skin to a predetermined percent strain. According to some variations, the step of straining skin on opposing sides of a treatment area comprises applying a compressive stress to the skin. According to some variations, the step of straining skin on opposing sides of a treatment area comprises applying a measured strain to the skin. According to some variations, the step of straining skin on opposing sides of a treatment area comprises applying a measured force to the skin. According to some variations, the step of straining skin on opposing sides of a treatment area comprises applying a tensile stress to opposite sides of longitudinal edges of a wound. According to some variations, the step of straining skin opposing sides of a treatment area comprises applying a measured strain to the skin on opposite sides of longitudinal edges of a wound. According to some variations, the step of straining skin opposing sides of a treatment area comprises applying a measured force to the skin on opposite sides of longitudinal edges of a wound.

According to other variations, a skin straining device comprises: a first straining element comprising a first skin attachment structure; a second straining element comprising a second skin attachment structure; a handle structure coupled to at least one of the first straining element and the second straining element, configured to move the first straining element with respect to the second straining element; and wherein the first attachment structure and second attachment structure are configured to be positioned on opposite sides of a skin treatment region, and wherein the first and second straining elements are each configured to move with respect to each other in a manner that changes a distance between the first attachment structure and the second attachment structure; and a measuring element configured to determine a measurement corresponding to amount of force applied to the skin region. According to some variations the measurement comprises a predetermined amount of strain applied to the skin. According to some variations, the measurement comprises a predetermined amount of compressive strain applied to the skin. According to some variations the measurement comprises a predetermined amount of tensile strain applied to the skin. According to some variations, the measurement comprises a predetermined amount of compressive force applied to the skin. According to some variations, the measurement comprises a predetermined amount of tensile force applied to the skin.

According to some variations, the device further comprises a dressing configured to be placed on a pre-strained skin region to maintain at least a portion of the strain. According to some variations, the device is further configured to apply a strain of at least about 20% to the skin region. According to some variations, the device is further configured to apply a strain of at least about 40% to the skin region. According to some variations, the straining structure comprises a first frame structure and the second straining structure comprises a second frame structure, wherein at least one of said first and second frame structures is configured to provide an area of space in which to guide positioning of a skin treatment region. According to some variations, the device further comprises a dressing removably coupled to the device, wherein the dressing is configured to be positioned on a skin region strained by the device. According to some variations, the first attachment structure and second attachment structure each comprise a plurality of attachment elements. According to some variations, each of the plurality of attachment elements of each of the first and second attachment structures provide a variable strain between an adjacent attachment element. According to some variations, the device further comprises a plurality of spring elements each of said plurality of spring elements positioned between adjacent attachment elements. According to some variations, the attachment structures comprise a skin adhesive.

BRIEF DESCRIPTION OF THE DRAWINGS

FIG. 1A is a superior view of a skin treatment device in a first position.

FIG. 2C is an inferior view of the skin straining device of FIG. 2A in the second position.

FIG. 3A is a superior view of a skin straining device and dressing assembly in a first position. FIG. 3B is a side elevational view of the device of FIG. 3A.

FIG. 5A is a perspective view of a skin stress unloading or straining device in a first position; FIG. 5B is a perspective view of the device of FIG. 5A in a second position.

DETAILED DESCRIPTION

Figure 1B:
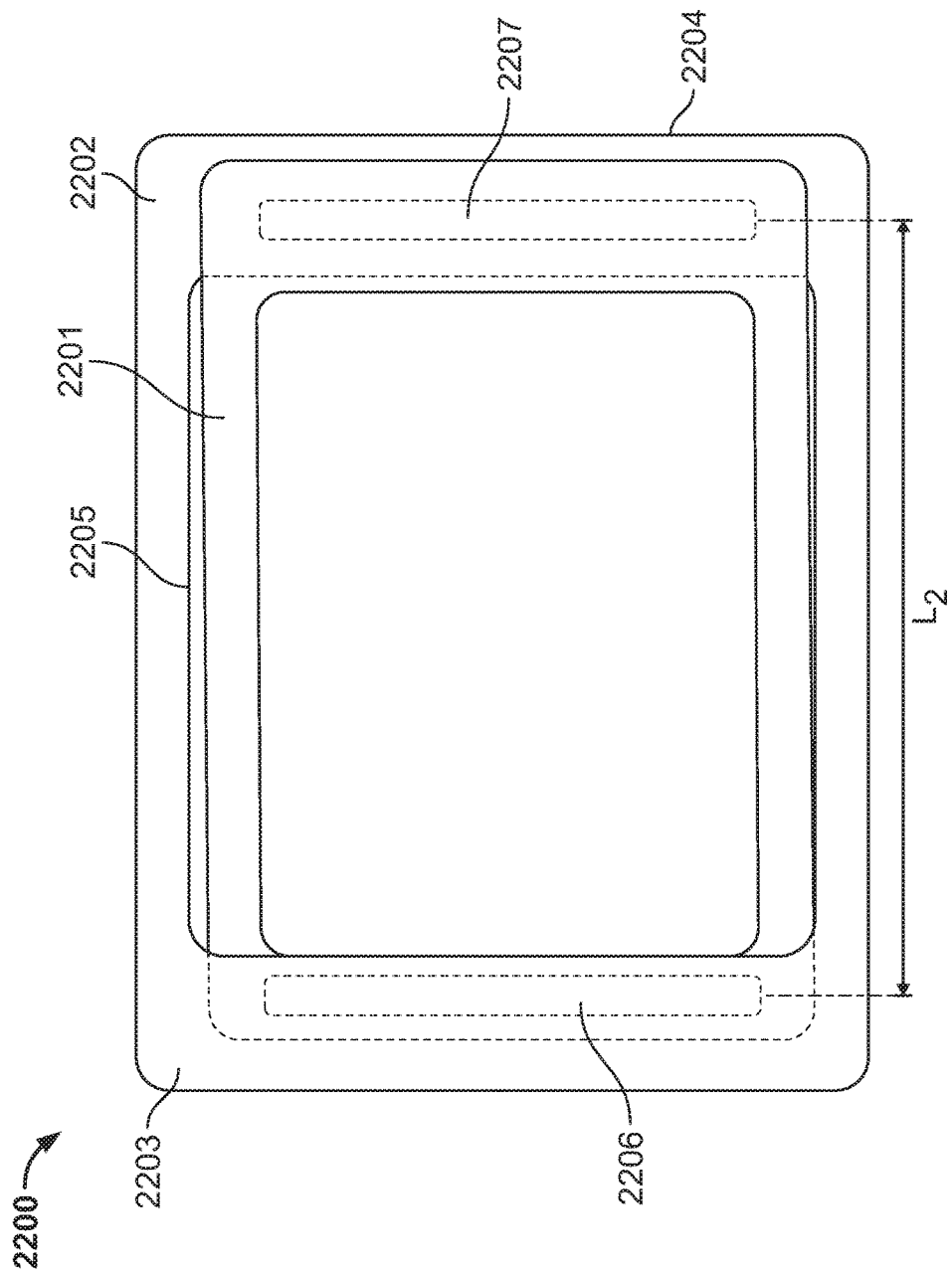
FIG. 1B is a superior view of the skin treatment device of FIG. 1A in a second position.

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, and methods described herein may control or regulate the mechanical environment of a wound to ameliorate scar and/or keloid formation. The mechanical environment of a wound includes stress, strain, and any combination of stress and strain. The control of a wound's mechanical environment may be active or passive, dynamic (e.g., by applying an oscillating stress) or static. The stresses and strains acting on the wound may involve the layers of the skin, such as the outer stratum corneum, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury. In general, scars typically have a triangular cross-section.

That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that mechanical strain acting on a wound or incision early in the proliferative phase of the wound healing process may inhibit cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids by offloading or neutralizing at least some of the strain that may be acting on the wound or incision. This tensile strain may be exogenous and/or endogenous strain, and may include but is not limited to the strain from the intrinsic tensile forces found in normal intact skin tissue.

Devices and methods are described herein for ameliorating the formation of scars and/or keloids at a wound site. The scars may be any type of scar, e.g., a normal scar, a hypertrophic scar, etc. In general, the devices may be configured to be removably secured to a skin surface near a wound. The devices may shield the wound from endogenous stress and/or exogenous stress. In some variations, the devices may shield the wound from endogenous stress without affecting exogenous stress on the wound, e.g., devices that modify the elastic properties of the skin, etc. In other variations, the devices may shield the wound from exogenous stress without affecting endogenous stress on the wound. Such variations may include situations where the musculature and surrounding wound tissue has been paralyzed, e.g., through the use of botulinum toxin or the like. In still other variations, the devices shield the wound from both endogenous and exogenous stress.

In such variations, a device may comprise a first device to temporarily exert forces that unload stresses or shield wounds from various stresses, and a second device to maintain at least some of such unloading or shielding for a period of time.

The devices described herein may ameliorate the formation of scars at wound sites by controllably stressing or straining the epidermis and deeper layers of dermal tissue around the wound, thereby reducing tensile or compressive stress at the wound site itself. The stress at the wound site may be reduced to levels below that experienced by normal skin and tissue. The stress or strain may be applied to surrounding tissue in one, two, or three directions to reduce endogenous or exogenous stress at the wound in one, two or three directions.

According to some variations of devices and methods herein, a first device may be used to compressively strain skin and then a second device may be used to hold or maintain at least a portion of the strain. According to variation of devices and methods herein a device used to strain skin may comprise a skin straining element and a strain holding element. According to variation of devices and methods herein, skin adjacent a wound or scar may be compressively stressed or strained to a desired or predetermined amount or force. According to some variations of devices and methods herein, skin adjacent a wound or scar may tensile stressed or strained to a desired or a predetermined amount or force. According to some variations of devices or methods herein, skin near a previously closed wound or incision, such as, a sutured wound or incision may be stressed or strained with the skin frame to unload stresses at the wound or incision site. A dressing may then be applied over stressed or strained skin to maintain at least a portion of the stress unloading or strain.

According to some variations of devices and methods herein as strain of greater than 10%, 20%, 30%, 40%, 50%, or 60% may be applied to an area of skin. A dressing applied to the skin may maintain greater than 90%, 80%, 70%, 60%, 50%, 40%, 30%, or 20% of the strain applied to the skin.

FIGS. 1A and 1B illustrate a skin frame 2200 configured to pre-strain skin prior to application of a skin treatment device to the skin that will hold the skin in a strained configuration. The frame 2200 comprises an inner sliding frame 2201 and an outer sliding frame 2202. Attachment structure 2206 is attached to the bottom of inner sliding frame 2201 on a first side 2203 of the skin frame 2200. Attachment structure 2207 is attached to the bottom of the outer sliding frame 2202 on a second side 2204 of the skin frame 2200. The attachment structures 2206, 2207 are configured to attach to skin, for example by way of adhesive, friction pads, microneedles and the like. The friction pads may comprise a silicone, a viscoelastic polymer such as styrenic block polymers, and the like. The skin frame 2200 may comprise a paperboard, plastic, rigid, semi-rigid or flexible material, including but not limited to, for example, a plastic, e.g., PVC or acrylic, or a paperboard. a laminate of a material, such as a solid bleach sulfate paperboard with a layer of flexible material between layers of paperboard, for example, silicone, polyurethane, low-density polyethylene or a rubber material. The material may also be a metal.

In use, the attachment structures 2206, 2207 are attached to skin when the skin frame is in the first position as shown in FIG. 1A. In the first position the distance between the attachment structures is L1. As shown in FIG. 1B, the sides 2203, 2204 of the skin frame are slid together by sliding inner frame 2201 and outer frame 2202 with respect to each other. Thus the distance between the attachment structures is L2 where L2 is less than L1, thus straining the skin to which the attachment structures 2206, 2207 are attached. A skin treatment device may then be placed through opening 2205 of the skin frame. The skin treatment device is configured to hold the skin in place. The skin treatment structure may be an unstrained or a strained treatment structure. For example such as the dressings, wound treatment device or skin treatment devices described herein or use with an applicator.

The skin frame 2200 may include a slot or guide rail on the underside or an inner window edge of the sliding outer frame 2202 on the first side of the skin frame 2200, that slidably couple the inner and outer frames 2201, 2202, for example. Alternatively, the slot or guide rail may be located on an inner window edge of the sliding outer frame 2202 that slidably couples to an outer edge of the inner frame 2201. The skin frame 2200 may also include a handle on the sliding inner frame 2201 on the first side 2203 of the skin frame 2200 for pulling or pushing the inner skin frame 2201 with respect to the outer skin frame 2202. A handle may also be provided on the sliding outer frame 2202 on the second side 2204 of the skin frame 2200 to assist in moving the inner and outer frames with respect to each other. Gripping surface material may also be provided on the handles or on the surfaces of the frame 2200 to facilitate squeezing of the frame 2200. The inside of the outer frame and/or the outside of the inner frame may be coated with a lubricious material such as Kapton tape or may be constructed of a low friction material such as HDPE or UHMWPE to permit ease of sliding.

The skin frame 2200 may be alternatively constructed where attachment structure 2206 is alternatively attached to the bottom of the inner sliding frame 2201 on the second side 2204 of the skin frame 2200 and attachment structure 2207 is alternatively attached to the bottom of the outer sliding frame 2202 on the first side 2203 of the skin frame 2200. In such a configuration FIG. 1B would represent a first configuration where the skin is not compressed by the skin frame. FIG. 1A would represent a second configuration in which skin is compressively strained between the inner sliding frame 2201 on the second side 2204 and the outer sliding frame 2202 on the first side 2203 by sliding the frames together to decrease the distance between attachment structures.

Referring to FIGS. 2A to 2F, another variation of a skin straining or compressing device 2300 is illustrated. The device 2300 comprises a skin compressing or straining portion 2310 comprising an outer frame structure 2311 and an inner frame structure 2331 that is slidable within the outer frame structure 2311, i.e., at least a portion of the inner frame structure is slidable within a slot or groove or rail of the outer frame structure and so that window portions of each of the inner and outer frame structures at least partially overlap as described herein. The outer frame structure 2311 includes sides 2312, 2313, 2314, 2315 that form a window portion 2316 through which a wound, incision, typically a closed wound incision, or scar or other area of treatment of a subject's skin may be viewed for placement of the skin frame. The outer frame structure 2311 may also include guides 2324 that may be used to position the wound or other skin area within the window portion 2316. The outer frame structure 2311 may also comprise markings 2325 to indicate a percent strain in the skin compression or other metrics or measurements indicating the amount of compression such as change in distance or length. The outer frame structure 2311 includes an opening or slot 2317 into or through which the inner frame structure 2331 may move or slide. The device 2300 may comprise a paperboard, plastic, rigid, semi-rigid or flexible material, including but not limited to, for example, a plastic, e.g., PVC or acrylic, or a paperboard, a laminate of a material, such as a solid bleach sulfate paperboard with a layer of flexible material between layers of paperboard, for example, silicone, polyurethane, low-density polyethylene or a rubber material. The material may also be a metal.

The inner frame structure 2331 includes a frame portion 2337 that slides or moves within the slot 2317. The inside of the slot and/or the outside of the inner frame may be coated with a lubricious material such as Kapton tape or may be constructed of a low friction material such as HDPE or UHMWPE to permit ease of sliding. Frame portion 2337 includes sides 2332, 2333, 2334, 2335 that form a window portion 2336 that at least partially overlaps window portion 2316 of the outer frame structure 2311 when the frame portion 2337 is positioned in the slot 2317. Inner frame structure 2331 also comprises a dressing carrier 2340 and a dressing 2342 separated from the frame portion 2337 by fold line 2341. The inner frame structure 2331 also comprises a straining handle or tab portion 2348 that is used to exert a compressive stressing or straining force to skin of a subject as described in more detail herein. The free end 2349 of the dressing carrier 2340 in this illustration acts as a straining handle or tab portion 2348 that is pulled to exert a compressive stressing or straining force as described in more detail herein.

Figure 2A:
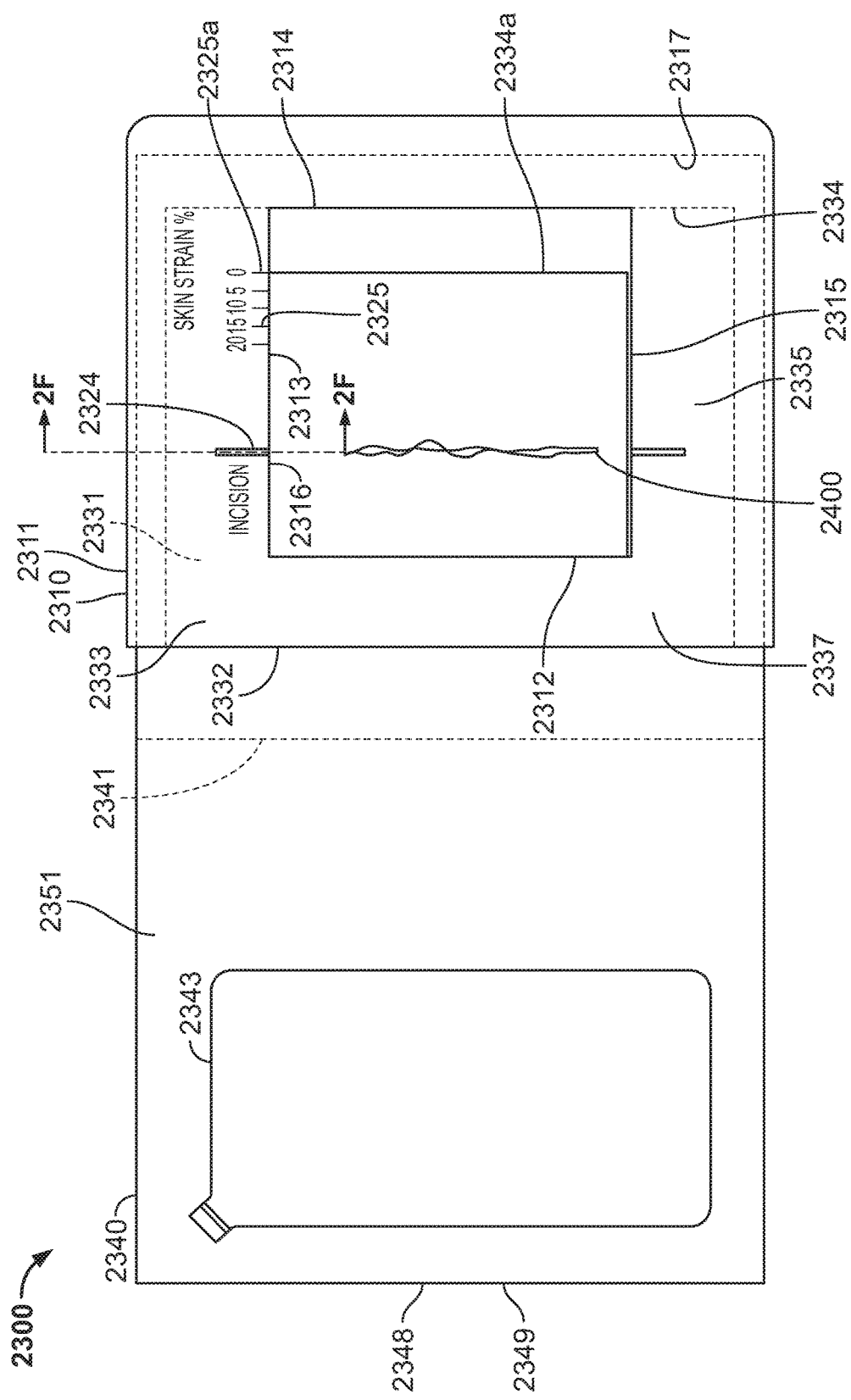
FIG. 2A is a superior view of a skin straining device and dressing assembly in a first position.

The dressing 2342 is positioned in a cut out or opening 2344 in the dressing carrier 2340. The opening 2344 is defined by sides 2345 which do not contact the dressing 2342. A liner 2343 overlays an adhesive side 2346 of the dressing on the top side 2351 of the inner frame structure 2331 as shown in FIG. 2A. The dressing 2342 is removably coupled to the dressing carrier 2340 by way of a frame wrapper 2352 which is positioned over the dressing 2342 and opening 2344 and is attached to the dressing carrier 2340 on the back side 2353 of the inner frame structure 2331. The adhesive side 2346 of the dressing 2342 includes a layer of a skin adhesive, such as, for example a pressure sensitive adhesive (PSA) to be applied to the skin of a subject. The adhesive side 2346 is covered by an adhesive liner 2343 located on the top side 2351 on the dressing carrier 2340. When removed, the adhesive liner 2343 exposes the adhesive layer 2346 of the dressing 2342 at the top side 2351 of the inner frame 2331.

The outer frame structure 2311 includes an attachment structure 2362 such as a skin adhesive on the side 2312 on the bottom side 2361 of the frame structure 2311. The attachment structure is constructed to removably attach the device 2300 to a first side of a wound or other skin location. The inner frame structure 2331 includes an attachment structure 2363 such as a skin adhesive on the side 2334 of the back side 2353 of the inner frame structure 2331. The side 2334 of the inner frame structure includes an edge 2334a that is exposed through window portion 2316 of the outer frame structure 2311. The attachment structures 2362, 2363 may be adhesives that are covered with a releasable liner prior to use.

The device 2300 is illustrated in FIG. 2A in a first initial configuration. In the initial configuration, the frame portion 2337 of the inner frame structure 2331 is positioned within the slot 2317 of the outer frame structure 2311 so that the edge 2334a of the side 2334 of the frame portion 2337 of the inner frame structure 2331 aligns with first marking 2325a. In this position the attachment structures 2362, 2363 are prepared to be applied to the skin of a subject e.g., in the case of an adhesive attachment structure, by removing an adhesive liner. The device 2300 is position on or over a wound or other treatment area of the skin of a subject by viewing the location of the wound or incision 2400 through the window portions 2316, 2336 of outer and inner frame structures 2311, 2331 respectively where the window portions 2316, 2336 overlap. The incision 2400 is positioned with its length aligned with markers 2324 on the top side 2360 of the outer frame structure 2311. The device 2300 is attached to the skin of the subject with attachment structures 2362, 2363 which are located on opposite sides of a wound, incision or other area to be treated 2400.

Figure 2B:
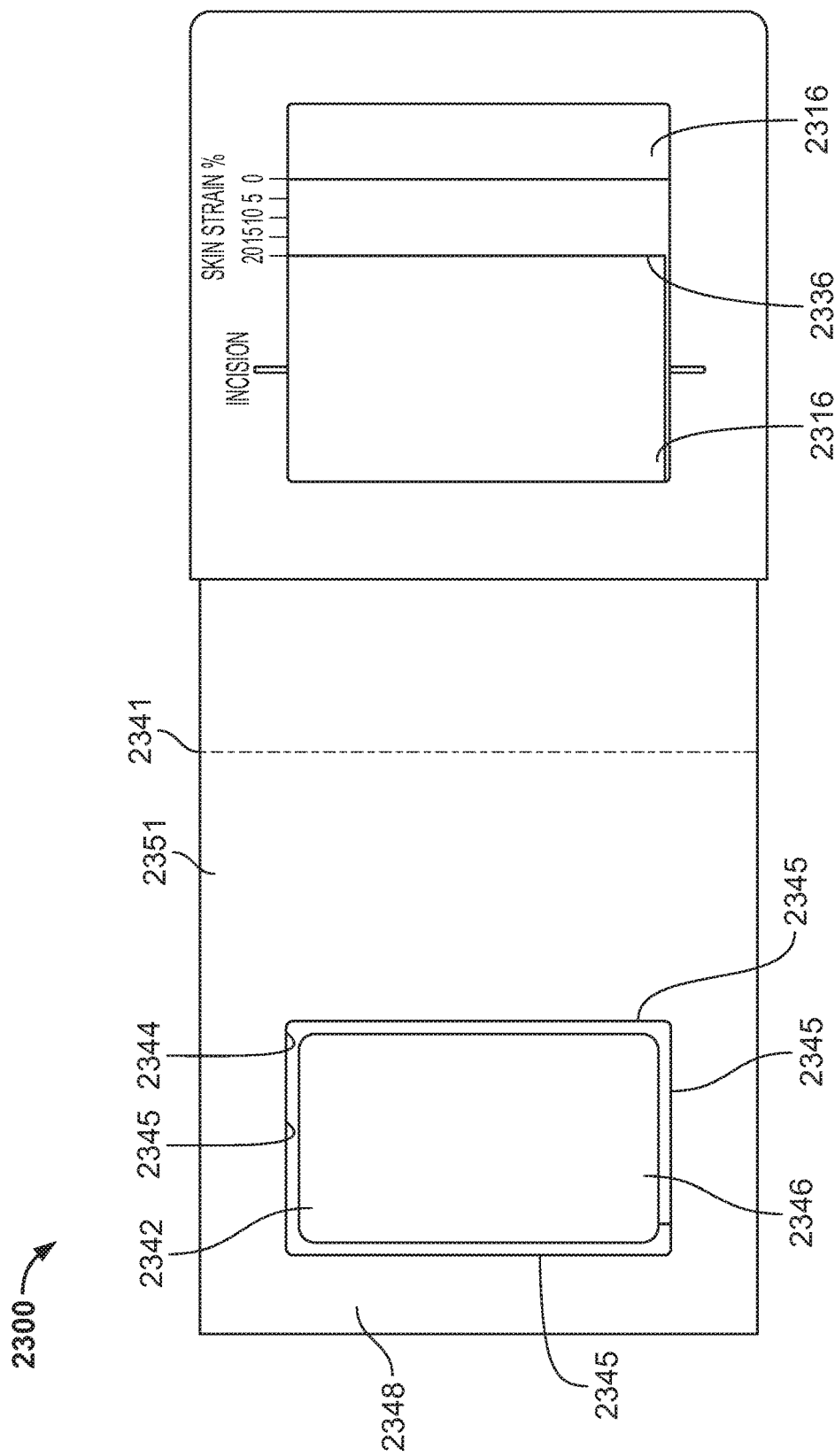
FIG. 2B is a superior view of the skin straining device of FIG. 2A in a second position.
Figure 2D:
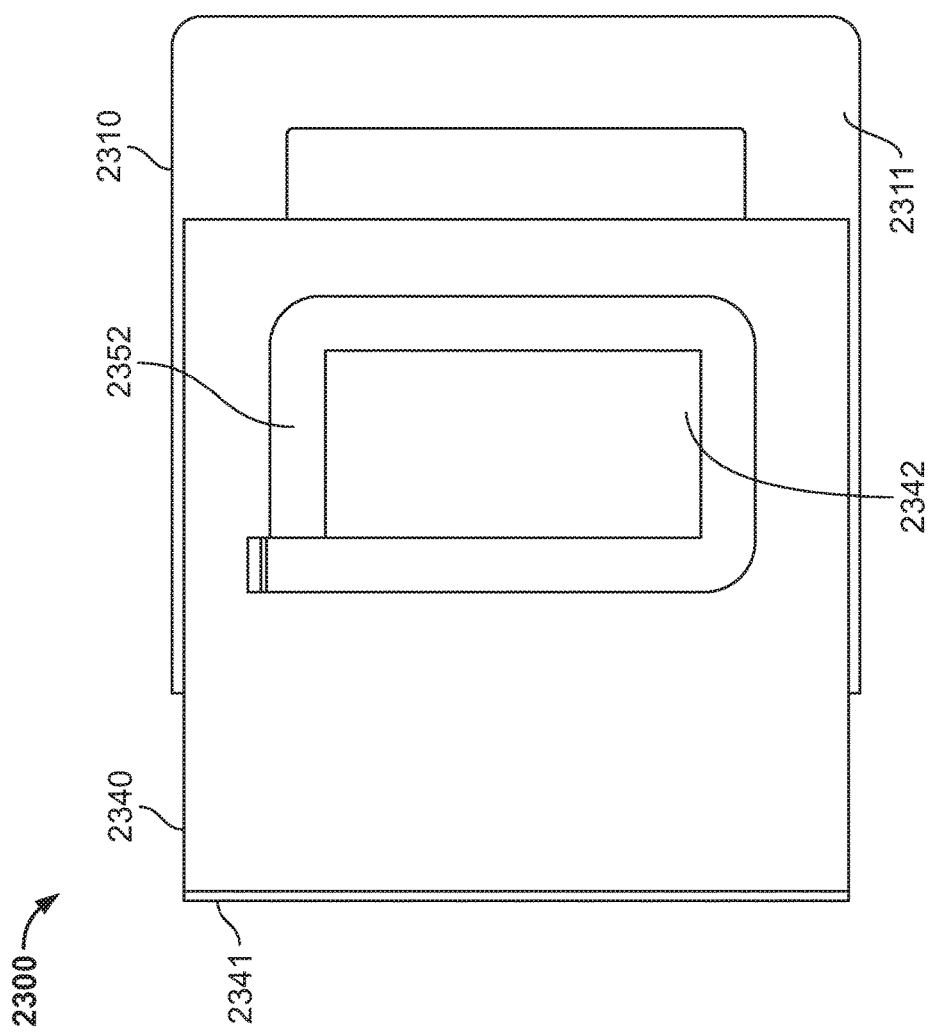
FIG. 2D is a superior view of the skin straining device of FIG. 2A in a third position in a first configuration.
Figure 2E:
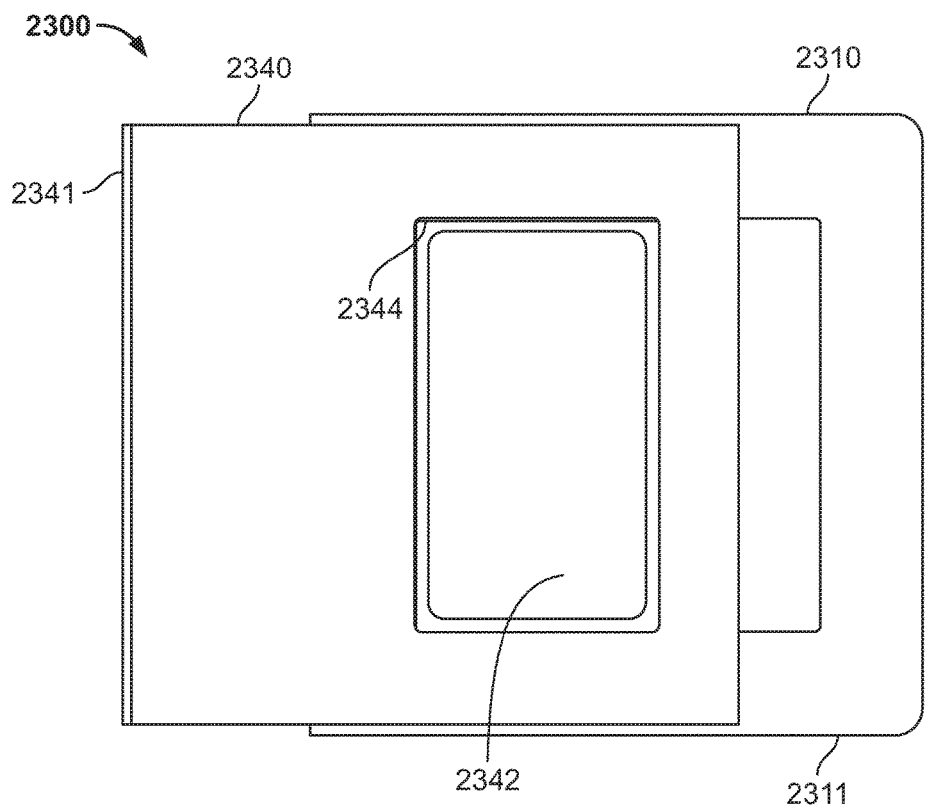
FIG. 2E is a superior view of the skin straining device of FIG. 2D in a second configuration.
Figure 2F:
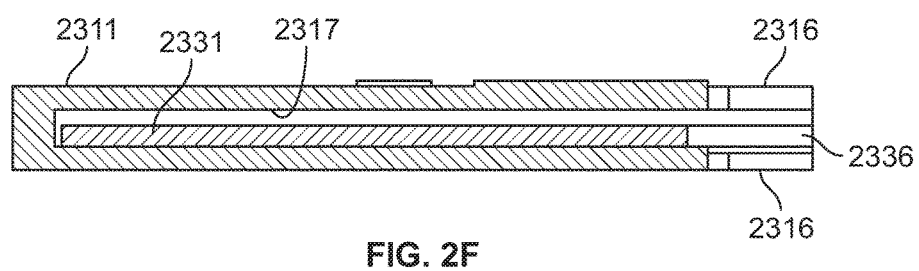
FIG. 2F is a cross sectional view of FIG. 2A along line A-A OF FIG. 2A.

As shown in FIG. 2B, the handle 2348 of inner frame structure 2331 is pulled to draw the side 2334 of the inner frame 2331 towards the side 2312 of the outer frame structure 2311. The sides 2334 and 2312, being attached to the skin, compress the skin together or compressively strain the skin when pulled together. Markings 2325 on the outer frame structure 2311 indicate the amount the skin has been pulled together by where the edge 2334a of the side aligns with the markings. As shown in FIG. 2B, the percentage of strain of the length of the skin between the sides 2312, 2334 is indicated. Such indications may be used to provide a predetermined, i.e., measured amount of force or strain as shown by the indications on the device. Alternatively, distance or change in distance between attachment structures may be indicated by the markings 2325. The adhesive liner 2343 of the dressing 2342 is removed to prepare the dressing 2342 for application to a compressed or strained area of skin.

When the skin has been compressed or strained to a desired degree, the dressing carrier 2340 is folded over at the fold line 2341 with the exposed adhesive 2346 of the dressing aligned with overlapping portions of the windows 2316, 2336, and is applied through the windows 2316, 2336 to the compressed skin. The dressing 2342 may then be released from the dressing carrier 2340 by removing the frame wrapper 2352 which holds the dressing 2342 to the dressing carrier 2340. The frame wrapper 2352 may be attached to the dressing carrier 2340 and/or the dressing 2342 for example, with a light tack adhesive, or a Mylar or polyester release liner that is already inherently tacky when placed on a silicone elastomer dressing. The frame wrapper may be constructed for example of an LPDE film or a paper liner. The frame wrapper 2352 has less adhesive strength than the attachment structures 2362, 2363 so that the frame wrapper 2352 may be removed without removing the attachment structures 2362, 2363 from the skin. After the frame wrapper 2352 is removed, the remaining elements of the device 2300 may then be removed from the patient by peeling the adhesive attachment structures 2362, 2363 off the skin of the subject leaving the dressing 2342 on the subject. The device 2300 may be disposed of after removal or it may be reloaded or reused with a new dressing.

FIGS. 3A and 3B illustrate a variation of a skin straining or compression device 3000. The device 3000 comprises an outer frame structure 3011 and an inner frame structure 3031 that is slidable with respect outer frame structure 3011. The device 3000 may comprise a paperboard, plastic, rigid, semi-rigid or flexible material, including but not limited to, for example, a plastic, e.g., PVC or acrylic, or a paperboard. a laminate of a material, such as a solid bleach sulfate paperboard with a layer of flexible material between layers of paperboard, for example, silicone, polyurethane, low-density polyethylene or a rubber material. The material may also be a metal.

The outer frame structure 3011 includes handle portion 3012, first compression arm 3013 and second compression arm 3014. The compression arms 3013, 3014 may further comprise or are coupled to generally parallel compression bands or bars 3113, 3114 respectively that are coupled to a series of compression bands 3115a, 3115b, 3115c and 3115d extending across compression bars 3113, 3114. The compression bands 3115a, 3115b, 3115c and 3115d include a skin adhesive layer on the underside for attaching to an area of skin to be compressed or strained. The compression bands 3115a, 311b, 3115c and 3115d are separated by spring members 3001, 3002, 3003 having spring rates, e.g., constants k1, k2 and k3 respectively. According to one variation k1>k2>k3. In other variations the spring constants may be equal or may vary in any manner as desired. The inner frame structure 3031 includes handle portion 3032, first compression arm 3033 and second compression arm 3034. The compression arms 3033, 3034 are coupled to generally parallel compression bars or bands 3133, 3134 respectively that are coupled to a series of compression bands 3135a, 3135b, 3135c and 3135d extending across compression bars 3133, 3134. Outer frame structure 3011 and inner frame structure 3031 are movably attached by the compression bars 3133, 3134 that are fixed to compression band 3135a and are slidably coupled to the compression bands 3115a, 3115b, 3115c, 3115d. For example, the compression bars 3133 and 3134 may extend through openings, slots or rails in compression bands 3115a, 3115b, 3115c, 3115d. The compression bands 3135a, 3135b, 3135c and 3135d include a skin adhesive layer 3055 on the underside for attaching to an area of skin to be compressed or strained. The compression bands 3135a, 3135b, 3135c and 3135d are separated by spring members 3004, 3005, 3006 having spring constants k3, k2 and k1 respectively. According to one variation k1>k2>k3. In other variations the spring constants may be equal or may vary in any manner as desired.

The inside of the outer frame and/or the outside of the inner frame may be coated with a lubricious material such as Kapton tape or may be constructed of a low friction material such as HDPE or UHMWPE to permit ease of sliding.

Compression bars 3133, 3134, and compression bands 3115d and 3135d form a window portion 3316 through which a wound, incision, scar or other area of treatment for a subject's skin may be viewed for placement of the skin frame. The inner frame structure 3031 also includes guides 3325 that may be used to position the wound or other skin area within the window portion 3316. The outer frame structure 3011 comprises markings 3324 to indicate the amount of compression in the skin that is positioned between bands 3115a and 3135a such as, e.g., a percent strain, change in distance or length when the outer frame structure 3011 and inner frame structure 3031 are moved with respect to each other. The band 3135d of the inner frame structure 3031 may be used to align with the markings 3324 of the outer frame structure 3011 to indicate amount of compression of skin within the window. Such markings or indications may be used to provide a predetermined, i.e., measured amount of force or strain as shown by the markings on the device.

The handle portions 3012 and 3032 of outer frame structure and inner frame structure respectively are used to exert a compressive stressing or straining force to skin of a by pulling the handles 3012, 3032 away from each other to draw bands 3115a, 3115b, 3115c or 3115d towards bands 3135a, 3135b, 3135c and 3135d to exert a compressive stressing or straining force to skin between bands 3115a and 3135a. The spring elements 3001, 3002, 3003, 3004, 3005, 3006 having varying rates act to controllably vary the compression between adjacent bands 3115a-d or 3135a-d. Thus compression may gradually be reduced or otherwise varied as the distance from the wound site increases.

The skin adhesive layers 3055 on the bands 3115a-d of the outer frame structure 3011 are configured to removably attach the bands 3115a-d to a first side of a wound or other skin location. The skin adhesive layers 3055 on the bands 3135a-d of the inner frame structure 3031 are configured to removably attach the bands 3135a-d a second side of a wound or other skin location. The adhesive layers 3055 may be covered with a releasable liner prior to use.

The device 3000 is illustrated in FIGS. 3A and 3B in a first initial configuration. In the initial configuration, the outer frame structure 3011 and the inner frame structure 3031 are positioned so that markers 3325 are aligned with the zero marking of the inner frame member indicating zero compression or strain. In this position the adhesive layers 3055 are prepared to be applied to the skin of a subject by removing one or more adhesive liners. The device 3000 is positioned on or over a wound or other treatment area of the skin of a subject by viewing the location of the wound through the window portions 3316. The incision is positioned with its length aligned with markers 3325 on the top side of the inner frame structure 3031. The device 3000 is attached to the skin of the subject with bands 3115a-d and 3135a-d.

The handles 3012, 3032 are pulled apart to draw bands 3135a-d of the inner frame structure 3031 towards the bands 3115a-d the outer frame structure 3011. Handles 3012, 3032 may include gripping features that may be used when they are pulled apart. The bands 3015a-d and 3135a-d being attached to the skin, compress the skin together or compressively strain the skin when pulled together. Markers 3324 on the outer frame structure 3011 indicate the amount the skin has been pulled together by alignment of markings 3324 with the band 3135d. Having varying spring constants, spring elements 3001, 3002, 3003, 3004, 3005, 3006 control the movement of the bands 3115a-d with respect to the bands 3135a-d so that a reduced amount of strain is progressively applied between bands so that the strain is reduced at progressively more outward bands with respect to the wound. Where spring constants are the same, the strain is reduced at the same rate between bands where the springs are positioned. A locking mechanism may be provided to maintain the inner and outer frame structures in place after pulling the handles apart. For example, bars 3033, 3034 may include ratchet structures that engage with features in openings, slots or rails in compression bands 3115a, 3115b, 3115c, 3115d.

When the skin has been compressed or strained to a desired degree, a dressing may be applied over the areas of skin between the bands 3115a-d and 3135a-d. After the device 3000 is removed, an additional dressing may be applied over the initial dressings to maintain at least some of the strain imparted to the skin by the device 3000. Alternatively, a dressing may be placed over the bands 3115a-d, 3135a-d and bands and springs 3001-3006 which are left in place while the remaining portion of the device 3000 (e.g., the handle portions 3012, 3032) may be removable or separable from the bands 3113, 3114, 3313, 3314, e.g., there may be a perforation or manufactured line of direction weakness between the handle 3012, 3032 and the bands 3115a, 3135a that can be severed separated or cut in a direction e.g. orthogonal to the direction of compression applied to the skin.

Figure 4A:
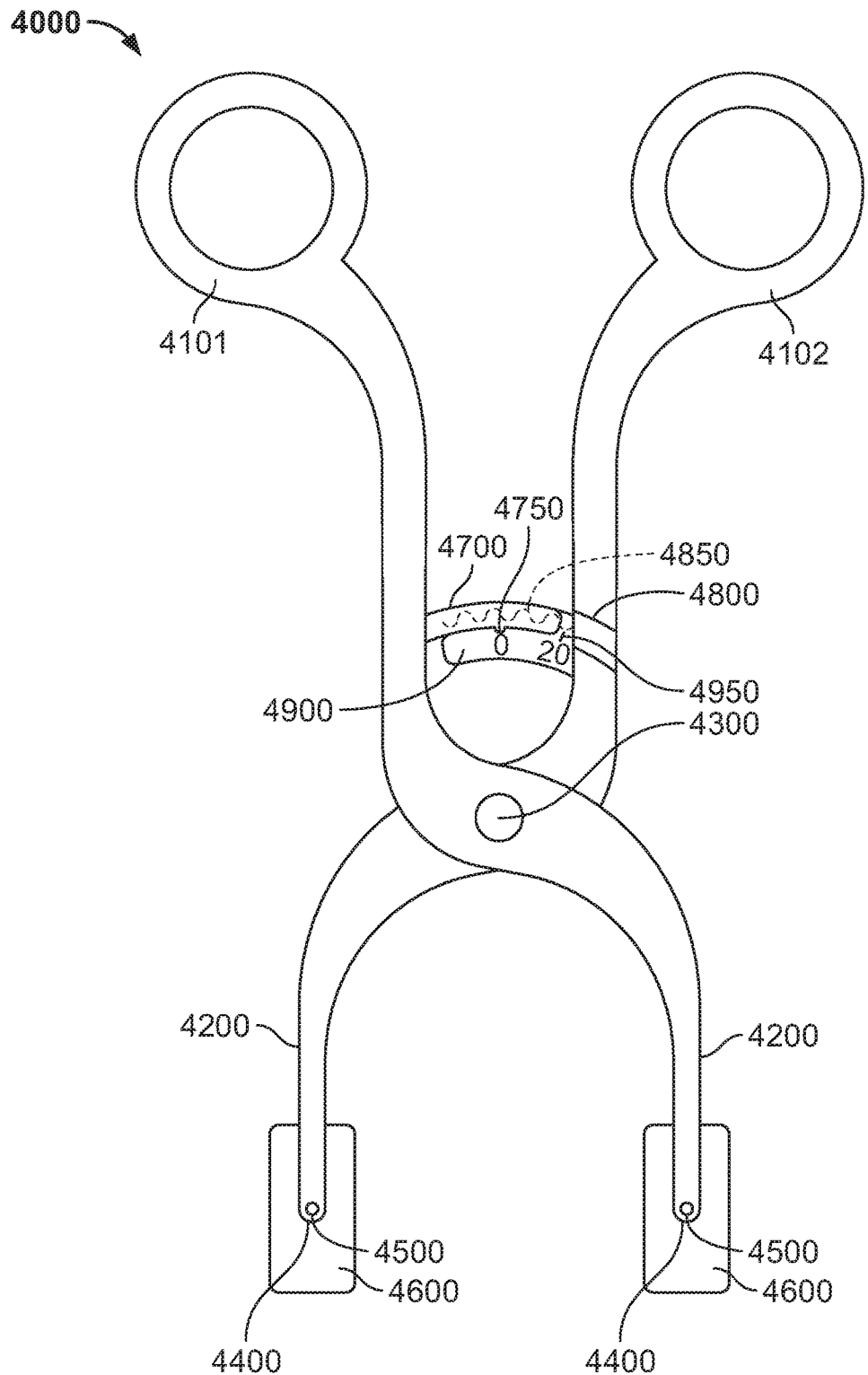
FIG. 4A is a superior view of a skin stress unloading or straining device in a first position.
Figure 4B:
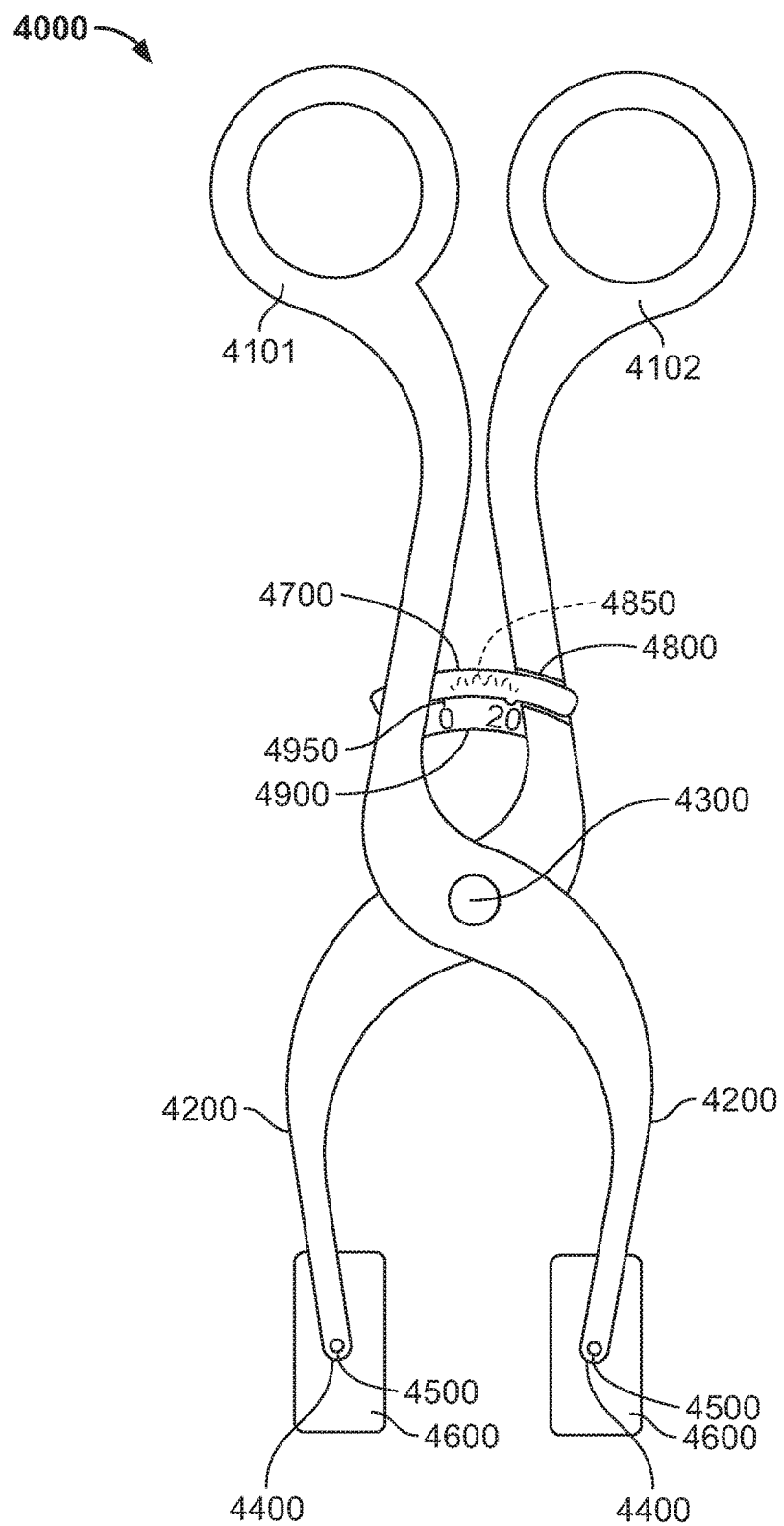
FIG. 4B is a superior view of the device of FIG. 4A in a second position.

Referring now to FIGS. 4A and 4B, a skin compressing device 4000 is illustrated. The device 4000 comprises opposing handle members 4101, 4102 that are pivotably attached by connector 4300 at a pivot point. Distal pivot arms 4200 extend from handle members 4101, 4102 and include attachment structures 4600 pivotably attached by pins 4500 at the ends 4400 of the distal pivot arms. According to some variations, the distance from the handle members 4101, 4102 to the connector 4300 or pivot point may be greater than the distance from the connector 4300 or pivot point to the attachment structures 4600 to provide a mechanical advantage at the handles. The attachment structures 4600 are configured to attach to the skin of a subject. The attachment structures 4600 may comprise, for example, a pressure sensitive adhesive. The handle members 4101, 4102 further comprise a measurement arm 4700 extending from a first handle member 4101 through a slot 4800 in a second handle member 4102. The measurement arm 4700 includes an indicator line 4750 that moves with handle. Markings 4950 on second measurement arm 4900 on the second handle 4102 represent the distance between the attachment structures 4600 when the handles 4101, 4102 are squeezed together and indicator line 4750 or the first measurement arm 4700 lines up with the handle 4102. The markings 4950 may also represent a percentage strain. The measurement arm 4900 may also comprise ratchets 4850 that engage with measurement arm 4700 and permit stepwise straining of the skin. The ratchets 4850 may also correspond with the markings 4950. Alternatively the attachment structures may have the force transducers shown in FIG. 5 A or 5B to show the amount of force applied to the skin when used. Such markings or indications may be used to provide a predetermined, i.e., measured amount of force or strain as shown by the indications on the device. For example, the predetermined amount of strain may be a predetermined absolute percentage of strain or level of force that is independent of the shape and/or size of the treatment site. As a further example, this absolute percentage of strain or level of force may be independent of the minimum strain or force to achieve sutureless wound closure (e.g. a relative strain or force to achieve opposition of the incision edges of a treatment site). Furthermore, the force needed to achieve wound closure is not a predetermined strain or force, since the final level of strain or force is not known until opposition of the incision edges is achieved.

In use, a wound or area to be treated is positioned between the attachment structures 4600. The handle members 4101, 4102 are squeezed together to a desired degree to apply a compressive or compressively straining force to the skin where the device 4000 is attached. As the attachment structures 4600 move together, the distal pivot arms 4200 may pivot at pivot pins 4500 with respect to the attachment structures 4600 so that the forces applied to the attachment structures 4600 remain generally parallel. A dressing may then be applied to the wound and or area of compressed skin to maintain or hold at least a portion of the stress and or strain applied by the device 4000, after which the device 4000 may be removed from the skin, leaving the dressing in place.

Referring to FIGS. 5A to 5B, a skin tensioning device 5000 is illustrated. The device 5000 comprises opposing handle members 5100 that are pivotably attached by connector 5300. Distal pivot arms 5200 extend from handle members 5100 and include attachment structures 5600 pivotably attached by pins 5500 at the ends 5400 of the distal pivot arms 5200. According to some variations, the distance from the handle members 5100 to the connector 5300 or pivot point may be greater than the distance from the connector 5300 or pivot point to the attachment structures 5600 to provide a mechanical advantage at the handles. The attachment structures 5600 are configured to attach to the skin of a subject. The attachment structures 5600 may comprise, for example, a pressure sensitive skin adhesive. The attachment structures 5600 further comprise force transducers 5700 that sense the amount of force or change in forces applied to the skin. The attachment structures 5600 further comprise electrical connectors 5800 electrically coupled to the force transducers 5700, and for connecting a reading device to read and/or display the forces sensed by the force transducers corresponding to amount of force applied or percent strain on the skin. The force transducers 5700 comprise deflectable portions 5750 and transverse portions 5775. The transverse portions 5775 include an adhesive on the bottom surface to attach to the skin in an orientation that is transverse to the attachment structures 5600. The deflection of the deflectable portions 5750 corresponds to a function of the transverse force acting on the skin between the attachment structures 5600. Such measurements made by the force transducer may be used to provide a predetermined, i.e., measured amount of force or strain as shown by the indications by the device.

In use, the attachment structures 5600 are positioned at the ends 5950 of a wound or area of skin to be treated 5900. The handle members 5100 are squeezed together to a desired degree which applies a separation, straining or tensile stressing force to the longitudinal edges of a wound 5950 adjacent which the attachment structures 5600 are attached. As the attachment structures 5600 separate, the distal pivot arms 5200 may pivot with respect to pivot pins 5500 so that the forces applied to the attachment structures 5600 are generally parallel. The forces applied along an axis of the wound creates compressive stresses transverse, e.g. to the axis of the wound to unload stresses at the wound site where the wound has been closed, e.g., according to Poisson's ratio. If the wound has not been closed, the forces in addition to unloading stresses at the wound site, may also draw the transverse edges of the wound together creating tissue apposition. A dressing may then be applied to the wound to hold at least a portion of the stresses applied by the device 5000 after which the device 5000 may be removed from the skin, leaving the dressing in place.

According to some variations of devices and methods herein, including but not limited to devices shown in the FIGS. 1A to 5B, the distance between adhesive regions attached to the skin may vary from region to region or may depend on a number of factors such as skin buckling, desired size of dressing, wound dimensions, among other things. According to some variations the distance between the adhesive regions may be between 5 and 15 mm, and/or between 9 and 11 mm.

The dressings described herein may include any skin treatment device, wound treatment device, scar or keloid treatment device, scar or keloid amelioration or prevention device, bandage, or dressing that may be applied, attached to or coupled to one or more layers of the skin of a subject. A dressing may be elastic or inelastic. The dressing may comprise for example, a material such as silicone, polyethylene, woven or non-woven polyurethane, Rayon or polyester.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

The invention claimed is:

1. A method of ameliorating scar formation in a treatment area wherein the treatment area comprises a previously closed wound of a skin of a subject, the method comprising:
    attaching a first skin attachment structure of a skin straining element adjacent a first longitudinal edge of a previously closed wound in the treatment area;
    attaching a second skin attachment structure of the skin straining element adjacent a second longitudinal edge of the previously closed wound in the treatment area, wherein the first longitudinal edge is opposing the second longitudinal edge;
    applying a tensile stress to opposite sides of the first and second longitudinal edges of the wound and causing a predetermined tensile force to the skin in the treatment area;
    coupling a strain holding element, comprising a dressing, to the skin treatment area and maintaining at least a portion of the force with the strain holding element by coupling an elastic element to the skin to hold a portion of the predetermined tensile force applied to the treatment area; and
    releasing the strain holding element and maintaining a resulting strain with the dressing for a treatment period.

2. The method of claim 1, wherein the step of causing a predetermined tensile force to skin in the treatment area comprises causing a predetermined tensile strain in skin in the treatment area.

3. The method of claim 2, wherein causing the predetermined tensile strain comprises causing a predetermined strain percent.

4. The method of claim 2, further comprising using the skin straining element to measure the predetermined tensile strain.

5. The method of claim 1, wherein maintaining at least the portion of the strain with the strain holding element comprises applying the dressing to at least a portion of the treatment area to maintain at least a portion of the strain for a treatment period.

6. The method of claim 1, wherein releasing the strain holding element comprises removing the first and second attachment structures and leaving the dressing in place for a treatment period.

7. The method of claim 1, wherein attaching the first skin attachment structure comprises attaching the first skin attachment structure to skin with a skin adhesive.

8. The method of claim 1, wherein one or more of the first and second skin attachment structures comprises a force transducer, and the method further comprises sensing an amount of force or change in force in the skin.

9. The method of claim 1, wherein applying a tensile stress to opposite sides of the first and second longitudinal edges of the wound comprises applying a separating force to the first and second longitudinal edges of the wound.

10. A method of ameliorating scar formation in a treatment area wherein the treatment area comprises a previously closed wound of a skin of a subject, the method comprising:
    attaching a first skin attachment structure of a skin straining element adjacent a first longitudinal edge of a previously closed wound in the treatment area;
    attaching a second skin attachment structure of the skin straining element adjacent a second longitudinal edge of the previously closed wound in the treatment area, wherein the first longitudinal edge is opposing the second longitudinal edge;
    applying a tensile stress to opposite sides of the first and second longitudinal edges of the wound by applying a separating force to the first and second longitudinal edges of the wound and causing a predetermined tensile force to the skin in the treatment area; and
    coupling a strain holding element to the skin treatment area and maintaining at least a portion of the force with the strain holding element.

11. The method of claim 10, wherein the step of causing a predetermined tensile force to skin in the treatment area comprises causing a predetermined tensile strain in skin in the treatment area.

12. The method of claim 11, wherein causing the predetermined tensile strain comprises causing a predetermined strain percent.

13. The method of claim 11, further comprising using the skin straining element to measure the predetermined tensile strain.

14. The method of claim 10, wherein maintaining at least the portion of the predetermined tensile force with the strain holding element comprises coupling an elastic element to the skin to hold a portion of the predetermined tensile force applied to the treatment area.

15. The method of claim 14, wherein the strain holding element comprises a dressing.

16. The method of claim 15, wherein maintaining at least the portion of the strain with the strain holding element comprises applying the dressing to at least a portion of the treatment area to maintain at least a portion of the strain for a treatment period.

17. The method of claim 15, further comprising releasing the strain holding element and maintaining a resulting strain with the dressing for a treatment period.

18. The method of claim 10, wherein attaching the first skin attachment structure comprises attaching the first skin attachment structure to skin with a skin adhesive.

19. The method of claim 10, wherein one or more of the first and second skin attachment structures comprises a force transducer, and the method further comprises sensing an amount of force or change in force in the skin.

* * * * *